United States Patent
Truschel et al.

(10) Patent No.: US 6,968,842 B1
(45) Date of Patent: Nov. 29, 2005

(54) MEASUREMENT OF A FLUID PARAMETER IN A PRESSURE SUPPORT SYSTEM

(75) Inventors: William A. Truschel, Monroeville, PA (US); Patrick W. Truitt, Pittsburgh, PA (US); Winslow K. Duff, Export, PA (US)

(73) Assignee: RIC Investments, Inc., Wilmington, DE (US)

( * ) Notice: Subject to any disclaimer, the term of this patent is extended or adjusted under 35 U.S.C. 154(b) by 130 days.

(21) Appl. No.: 10/402,541

(22) Filed: Mar. 28, 2003

Related U.S. Application Data (60) Provisional application No. 60/369,833, filed on Apr. 3, 2002.

(51) Int. Cl.$^7$ ............................................. A61M 16/00
(52) U.S. Cl. ........................... 128/204.18; 128/204.21; 128/204.23
(58) Field of Search ...................... 128/204.18, 204.21, 128/204.23, 204.22, 202.22, 848

(56) References Cited

U.S. PATENT DOCUMENTS

| | | | |
|---|---|---|---|
| 2,915,056 A * | 12/1959 | Lee .............................. | 128/29 |
| 4,083,245 A | 4/1978 | Osborn | |
| 4,796,651 A | 1/1989 | Ginn et al. | |
| 5,038,621 A | 8/1991 | Stupecky | |
| 5,443,061 A | 8/1995 | Champain et al. | |
| 5,694,923 A * | 12/1997 | Hete et al. .............. | 128/204.18 |
| 5,715,812 A | 2/1998 | Deighan et al. | |
| 5,740,795 A | 4/1998 | Brydon | |
| 5,743,270 A | 4/1998 | Gazzara et al. | |
| 5,868,133 A * | 2/1999 | DeVries et al. ......... | 128/204.21 |
| 6,029,660 A * | 2/2000 | Calluaud et al. ....... | 128/203.12 |
| 6,138,675 A * | 10/2000 | Berthon-Jones ......... | 128/204.23 |
| 6,212,435 B1 * | 4/2001 | Lattner et al. .............. | 607/134 |
| 6,401,713 B1 * | 6/2002 | Hill et al. ............... | 128/204.21 |
| 6,644,310 B1 * | 11/2003 | Delache et al. ......... | 128/204.21 |
| 6,644,311 B1 * | 11/2003 | Truitt et al. ............. | 128/204.22 |
| 6,768,279 B1 * | 7/2004 | Skinner et al. .............. | 318/254 |
| 6,817,361 B2 * | 11/2004 | Berthon-Jones et al. ...................... | 128/204.18 |

* cited by examiner

*Primary Examiner*—Henry Bennett
*Assistant Examiner*—Dinnatia Doster-Greene
(74) *Attorney, Agent, or Firm*—Michael W. Haas (57) ABSTRACT

A pressure support system has a motor, a switching element that supplies power to motor windings, and a blower coupled to the motor. Rotation of the blower elevates a pressure of fluid in a patient circuit coupled to an outlet of the blower. A rotational speed controller maintains the motor at a set rotational speed corresponding to a selected pressure for the fluid in the patient circuit. The rotational speed of the motor is maintained by a switching signal provided by a rotational speed controller to the switching element to control the actuation of the switching element. A fluid parameter monitoring portion monitors a parameter associated with the flow of fluid in the patient circuit, such as the magnitude, direction, or volume, based on a characteristic, such as duty cycle, of the switching signal, or based on a characteristic of a control signal that is used to generate the switching signal.

26 Claims, 5 Drawing Sheets

MEASUREMENT OF A FLUID PARAMETER IN A PRESSURE SUPPORT SYSTEM

CROSS-REFERENCE TO RELATED APPLICATIONS

This application claims priority under 35 U.S.C. § 119(e) from provisional U.S. patent application No. 60/369,833 filed Apr. 3, 2002.

BACKGROUND OF THE INVENTION

1. Field of the Invention

The present invention relates to a pressure support system and to a method of using such a system, and, more particularly, to a pressure support system and method in which a parameter associated with the fluid flow in a patient circuit, such as the magnitude of flow, direction of flow, or volume of fluid passing through the patient circuit, are monitored based on a characteristic of a signal used to control a motor in a pressure generating portion of the pressure support system.

2. Description of the Related Art

It is well known to treat a breathing disorder, such as obstructive sleep apnea (OSA), with a pressure support device, such as a continuous positive airway pressure (CPAP) device. A CPAP device delivers a flow of fluid to the airway of the patient throughout the patient's breathing cycle in order to "splint" the airway, thereby preventing its collapse during sleep. The term "fluid" as used herein refers to any gas, including a gas mixture or a gas with particles, such as an aerosol medication, suspended therein. Most commonly, the fluid delivered to a patient by a pressure support system is pressured air. An example of such a CPAP device is the REMstar® and Solo® family of CPAP devices manufactured by Respironics, Inc. of Pittsburgh, Pa.

It is also known to provide a bi-level positive pressure therapy in which the pressure of fluid delivered to the patient's airway varies or is synchronized with the patient's breathing cycle to maximize the therapeutic affect and comfort to the patient. An example of a pressure support device that provides "bi-level" pressure support, in which a lower pressure is delivered to that patient during the patient's expiratory phase than during the inspiratory phase, is the BiPAP® family of devices manufactured and distributed by Respironics, Inc. of Pittsburgh, Pa. Such a bi-level mode of pressure support is taught, for example, in U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the contents of each of which are incorporated by reference into the present invention.

It is further known to provide an auto-titration positive pressure therapy in which the pressure provided to the patient changes based on the detected conditions of the patient, such as whether the patient is snoring or experiencing an apnea, hypopnea, or upper airway resistance. An example of a device that adjusts the pressure delivered to the patient based on whether or not the patient is snoring is the Virtuoso® CPAP family of devices manufactured and distributed by Respironics, Inc. An example of a pressure support device that actively tests the patient's airway to determine whether obstruction, complete or partial, could occur and adjusts the pressure output to avoid this result is the Tranquility® Auto CPAP device, also manufactured and distributed by Respironics, Inc. An exemplary auto-titration pressure support mode is taught, for example, in U.S. Pat. Nos. 5,203,343; 5,458,137 and 6,087,747 all to Axe et al., the contents of which are incorporated herein by reference. A further example of an auto-titration pressure support device that actively tests the patient's airway to determine whether obstruction, complete or partial, could occur and adjusts the pressure output to avoid this result is the Tranquility® Auto CPAP device, also manufactured by Respironics, Inc. This auto-titration pressure support mode is taught in U.S. Pat. No. 5,645,053 to Remmers et al., the content of which is also incorporated herein by reference.

In each of these pressure support systems, it is often desirable to measure the flow of fluid to or from the patient, the volume of fluid delivered to or received from the patient, or both with a relatively high degree of accuracy. One reason for doing so is to monitor whether the patient is using, i.e., complying, with a prescribed pressure support therapy. If the pressure support device is operating, yet there are no variations in the flow of fluid delivered to the patient, which would normally be present as a result of patient breathing, it can be assumed that the patient is not actually receiving the flow of fluid. This may occur, for example, if the patient is not wearing the patient interface device that communicates the flow of fluid to his or her airway so that he or she is not receiving the therapeutic benefits of the pressure support treatment.

In a bi-level pressure support device it is desirable to monitor the flow of fluid delivered to the patient via a patient circuit to detect when the patient is spontaneously changing from the inspiratory phase to the expiratory phase of the breathing cycle and vice versa. Proper detection of transitions between the inspiratory phase and the expiratory phase are necessary in order to trigger the pressure support device at the end of the patient's expiratory phase and to cycle the device at the end of the inspiratory phase.

In an auto-titration pressure support system, monitoring the flow of fluid, the volume of fluid, or both is done to detect disordered breathing. For example, monitoring the flow of fluid in the patient circuit can be used to determine whether the patient is experiencing snoring, apnea, hypopnea, cheynes-stokes breathing, or other breathing abnormalities, as well as normal breathing patterns.

Various approaches for measuring the flow of fluid, the volume of fluid, or both in the patient circuit portion of a pressure support device are well known. For example, it is known to use a pneumatach flow meter placed directly in the patient circuit to measure the flow of fluid in the patient circuit. Examples of a conventional flow or volume measuring techniques are taught, for example, in U.S. Pat. No. 4,083,245 to Osborn; U.S. Pat. No. 4,796,651 to Ginn et al.; U.S. Pat. No. 5,038,621 to Stupecky; and U.S. Pat. No. 5,743,270 to Gazzara et al.

Because this flow/volume measurement techniques requires placing a flow element in the patient circuit, as well as providing a mass flow or pressure sensor associated with the flow element, it increases the cost of the pressure support system as well as its complexity. In some direct flow measurement devices, the flow element is specifically designed to provide the desired flow measurement capabilities, which also increases the cost and complexity of the flow meter design. Furthermore, the flow element is a flow restriction in the patient circuit, thereby decreasing the efficiency of the pressure support system.

Other techniques for sensing the flow of fluid communicated between a patient by a pressure support system are also known. For example, U.S. Pat. No. 5,443,061 to Champain et al. discloses a pressure support device that is capable of detecting variations in a drive current supplied to a motor that drives a blower in the pressure generating system. The system in Champain adjusts the drive current to modulate the pressure of the fluid at a mask in response to the patient's breathing cycle. U.S. Pat. No. 5,715,812 also to Deighan et al. discloses a current monitor coupled with the blower motor of a medical ventilator. The current monitor determines whether the patient is breathing into the patient circuit based on the current provided to the motor. Finally, U.S. Pat. No. 5,740,795 to Brydon discloses a pressure support system that senses the current or the power (voltage×current) provided to an electric motor to determine when a patient transitions between the inspiratory or expiratory phases of a breathing cycle. Brydon further teaches that the actual, volumetric flow of patient respiration can be determined from the measured current or power provided to the electric motor.

The monitoring systems taught by the patents noted above, however, do not quantitatively measure the flow of fluid or the volume of fluid in the patient circuit based on the monitored parameters unless they also include separate components for sensing at least the current or power provided to the motor. That is, the devices taught in these patents cannot determine the actual (quantitative) value of the flow of gas in the patient circuit or the quantitative volume of gas passing therethrough unless they include additional components to detect motor current or power. Those skilled in the art can appreciate that the use of such current sensors increases the cost and complexity of the pressure support system.

In summary, disadvantages of the above-described conventional devices for monitoring fluid flow/volume in a pressure support system depend upon the use of external sensors, such as motor current sensors, pressure transducers, heat sensors, position sensors, pressure switches, and the like, to provide an indication of the patient's interaction with the medical ventilator. While indirect flow sensing devices may be able to distinguish between patient inspiration and expiration or monitor patient usage, they cannot quantitatively measure the flow or volume of fluid delivered to or received from the patient unless they include a motor current sensing system or other conventional flow sensor. Of course, this additional current or flow sensor and associated circuitry adds cost and complexity to such devices.

SUMMARY OF THE INVENTION

Accordingly, it is an object of the present invention to provide a pressure support system that overcomes the shortcomings of conventional pressure support systems. In particular, it is an object of the present invention to provide a pressure support system that provides all of the functions of a flow meter placed directly in the patient circuit, such as determining the quantity and/or direction of flow in the patient circuit or the volume of fluid passing through a patient circuit in the pressure support system without the use of external sensors and associated instrumentation, such as a current sensor or a flow meter placed directly in the patient circuit.

These objects are achieved according to one embodiment of the present invention by providing a pressure support system that includes a motor having a plurality of phase windings. A switching element selectively supplies electrical power from a power source to the phase windings of the motor. A blower is coupled to the motor such that rotation of the blower by the motor elevates a pressure of fluid at an outlet of the blower. A patient circuit is coupled to an outlet of the blower to communicate the pressurized fluid with an airway of a patient. The pressure support system of the present invention includes a rotational speed controller that maintains a rotational speed of the motor at a set rotational speed, which corresponds to a speed necessary to provide a selected pressure for the fluid in the patient circuit. The rotational speed of the motor is maintained at the set rotational speed as a flow of fluid in the patient circuit changes by controlling a characteristic, such as the duty cycle, of a signal that controls the actuation of the switching element. A fluid parameter monitoring portion of the pressure support system monitors a parameter associated with the flow of fluid in the patient circuit based on this characteristic of the signal from the rotational speed controller. For example, the fluid parameter measuring portion can determine the quantity of flow in the patient circuit, the quantitative volume of fluid flow in the patient circuit, the direction of flow or any combination thereof.

It is a further object of the present invention to provide a method of providing pressure support to a patient that does not suffer from the above-described disadvantages of conventional pressure support techniques. This object is achieved according to the present invention by providing a method of operating a pressure support system having a motor coupled to a blower which is coupled in fluid communication with a patient via a patient circuit. The method includes producing a first signal that causes the motor to drive the blower at a set rotational speed to produce an elevated pressure for fluid in the patient circuit. The actual rotational speed of the blower is measured and a rotational speed error signal is determined as a difference between a set rotational speed corresponding to a selected pressure for the fluid in the patient circuit and the actual rotational speed of the blower. The method further includes adjusting a characteristic of the first signal, such as its duty cycle, based on the rotational speed error signal so that the motor drives the blower at the set rotational speed despite variations in the flow of the fluid in the patient circuit. A parameter associated with the flow of fluid in the patient circuit, such as the magnitude of the flow or the volume of fluid traversing or returning therethrough, is quantitatively determined based on this characteristic of the control signal. In addition, the direction of fluid flow in the patient circuit can be determined.

By measuring, for example, the quantity of the flow of fluid in the patient circuit based on the characteristic of the control signal, the present invention avoids the need for dedicated flow measuring or current sensing elements, thereby decreasing the cost and complexity of the pressure support system. This flow information can be used in the same manner as the flow information provided by a conventional flow sensor placed in the patient circuit. For example, the flow information provided by the flow sensing technique of the present invention can be used to measure quantitatively the volume of fluid flow over time, to determine the direction of flow in the patient circuit, to monitor the condition of the patient, to trigger or cycle the pressure support system, to monitor patient usage of the system, and to control the pressure provided to the patient, all without the need for specialized flow measuring or current sensing equipment.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EXEMPLARY EMODIMENTS

A. Pressure Support System Hardware

The general configuration of a pressure support system 2 in accordance with the principles of the present invention is described in below with reference to FIG. 1. More specifically, pressure support system 2 is capable of performing quantitative flow or volume measurements without the need for a dedicated flow element, as required in conventional pressure support systems.

Figure 1:
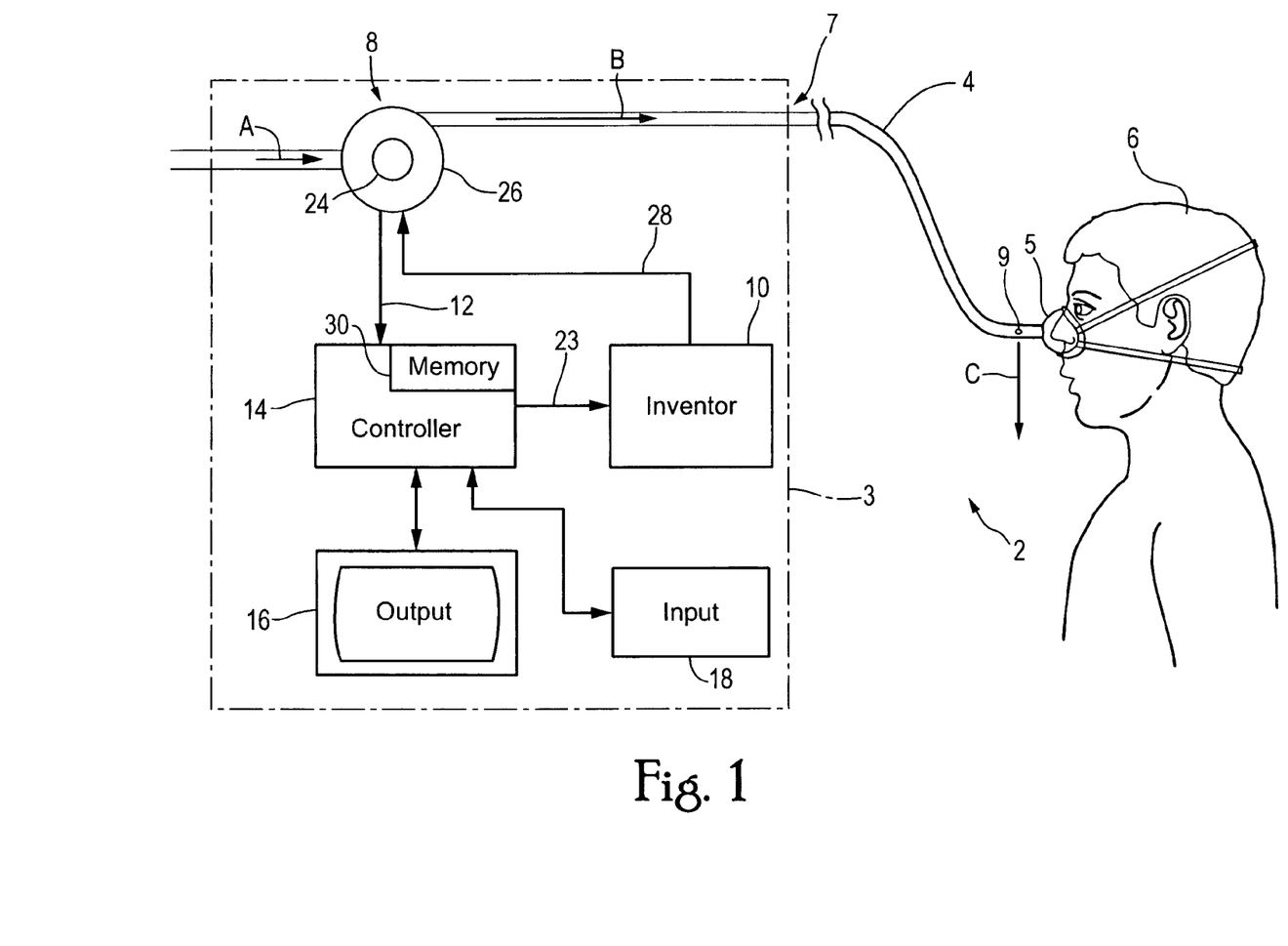
FIG. 1 is a schematic illustration of a pressure support system in accordance with the principles of the present invention.

Pressure support system 2 includes a patient circuit 4 configured to connect a patient 6 with the output of a pressure generator, which is generally indicated by numeral 8 in FIG. 1. Pressure generator 8 receives fluid, such as breathing gas, from a source of breathing gas, such as ambient atmosphere or a storage tank, as indicated by arrow A, and elevates the pressure of the gas at its output. Typically, this elevated pressure at the outlet of the pressure generator causes a flow of fluid, as indicated by arrow B, to occur in patient circuit 4. Patient circuit 4 communicates this flow of fluid to the airway of patient 6. In a preferred embodiment of the present invention, pressure generator 8 is a mechanical pressure generator, such as a blower, bellows or piston, that receives ambient air, for example, at an inlet from the gas source.

Patient circuit 4 preferably includes a short portion that carries fluid from the output of pressure generator 8 to an external coupling, generally indicated at 7, on a housing 3 containing the components of pressure support system 2. Housing 3 is schematically illustrated in FIG. 1 by a dashed line surrounding the components of the pressure support system contained in the housing. Patient circuit 4 also includes a flexible conduit portion that is attached to external coupling 7 of the housing. The flexible conduit carries the fluid from the pressure generator to an airway of the patient.

A patient interface device 5 at the end of the patient circuit communicates the flow of fluid in the patient circuit with the airway of the patient. The present invention contemplates that patient interface device 5 is any device suitable for communicating an end of patient circuit 4 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

Because patient circuit 4 is a single-limb circuit, i.e., it has only on conduit communicating the flow of breathing gas with the airway of the patient, it includes an exhaust element 9 to exhaust gas, such as the patient's exhaled gas, from the otherwise closed system. This flow of exhaust gas is indicated by arrow C in FIG. 1. The present invention contemplates providing the exhaust element in the patient circuit, on the patient interface device, or at both locations. Examples of conventional exhaust elements are described, for example, in U.S. Pat. No. Re. 35,339 to Rappoport; U.S. Pat. No. 5,937,855 to Serowski et al.; U.S. Pat. No. 6,112,745 to Lang; and published PCT application nos. WO 00/78381 to Gunaratnam et al. and WO 98/34665 to Kwok.

It is to be understood that various other components may be provided in or coupled to patient circuit 4. For example, a bacteria filter, pressure control valve, flow control valve, sensor, meter, pressure filter, humidifier and/or heater can be provided in or attached to the patient circuit. Likewise, other components, such as sensors, muffler and filters can be provided at the inlet of pressure generator 8.

Although not shown in FIG. 1, the present invention also contemplates providing a secondary flow of gas in combination with the primary flow of gas from atmosphere. For example, a flow of oxygen from any suitable source can be provided upstream to the inlet of pressure generator 8 or downstream of the pressure generator, e.g., in patient circuit 4 or at the patient interface device, to control the fraction of inspired oxygen delivered to the patient.

Pressure generator 8 includes a motor 24 that drives a blower 26. Preferably, motor 24 is a brushless DC (BLDC) motor that is connected to receive an armature current 28 from a switching element, such as an inverter 10. In an exemplary embodiment of the present invention, pressure generator 8 includes a sensor that detects the rotational speed of the motor, such as a tachometer sensor 38 schematically shown in FIG. 2A, and that provides a tachometer signal 12 to a controller 14. Those skilled in the art can appreciate that the rotational speed sensing function of a tachometer can be incorporated into controller 14 and need not be hardware sensor physically coupled to the pressure generator. Controller 14 operates in accordance with a software program stored in a memory 30 to provide to inverter 10 switching signals 23, which are determined based on drive signals 20 and control signals 22 as discussed in detail below.

Switching signals 23 cause inverter 10 to selectively supply armature current 28 to the motor in pressure generator 8 in a manner to be described hereinafter in greater detail. In response to the selective receipt of armature current 28, pressure generator 8 supplies fluid, such as air, oxygen, or an oxygen mixture, to patient circuit 4 and, hence, to patient 6. In operation, the tachometer sensor associated with pressure generator 8 outputs tachometer signal 12 that controller 14 utilizes as a feedback signal to control the application power to pressure generator 8 by means of switching signals 23. Thus, controller 14, more specifically, its associated components, operate as a means to control the rotational speed of the motor by controlling the actuation of the switching element that provides power to the motor in the proper sequence for the number of phase windings of the motor.

In an exemplary embodiment of the present invention, pressure support system 2 further includes an output device 16 and an input device 18 connected to controller 14 that provides an interface between controller 14 and an operator or patient 6. This enables information, data and/or instructions and any other communicatable items, collectively referred to as "data", to be communicated between a user and controller 14. Examples of conventional input devices suitable for this purpose include a keypad, buttons, switches, or keyboard. Examples of conventional output devices suitable for use with the present invention include a display, lights or other visual indicia or an audio-based device, such as a speaker.

It is to be understood that other communication techniques, either hard-wired or wireless, are also contemplated by the present invention as input/output devices. For example, the present invention contemplates providing a smart card terminal that enables data to be loaded into controller 14 from the smart card or loaded onto the smart card from the controller. Other exemplary interface devices and techniques adapted for use with the pressure support system include, but are not limited to, an RS-232 port, CD reader/writer, DVD reader/writer, RF link, modem (telephone, cable or other). In short, any conventional technique for providing, receiving, or exchanging data with controller 14 are contemplated by the present invention as input/output devices 16 and 18.

B. Operation of the Pressure Support System

1. Operation of the Controller

Figure 2A:
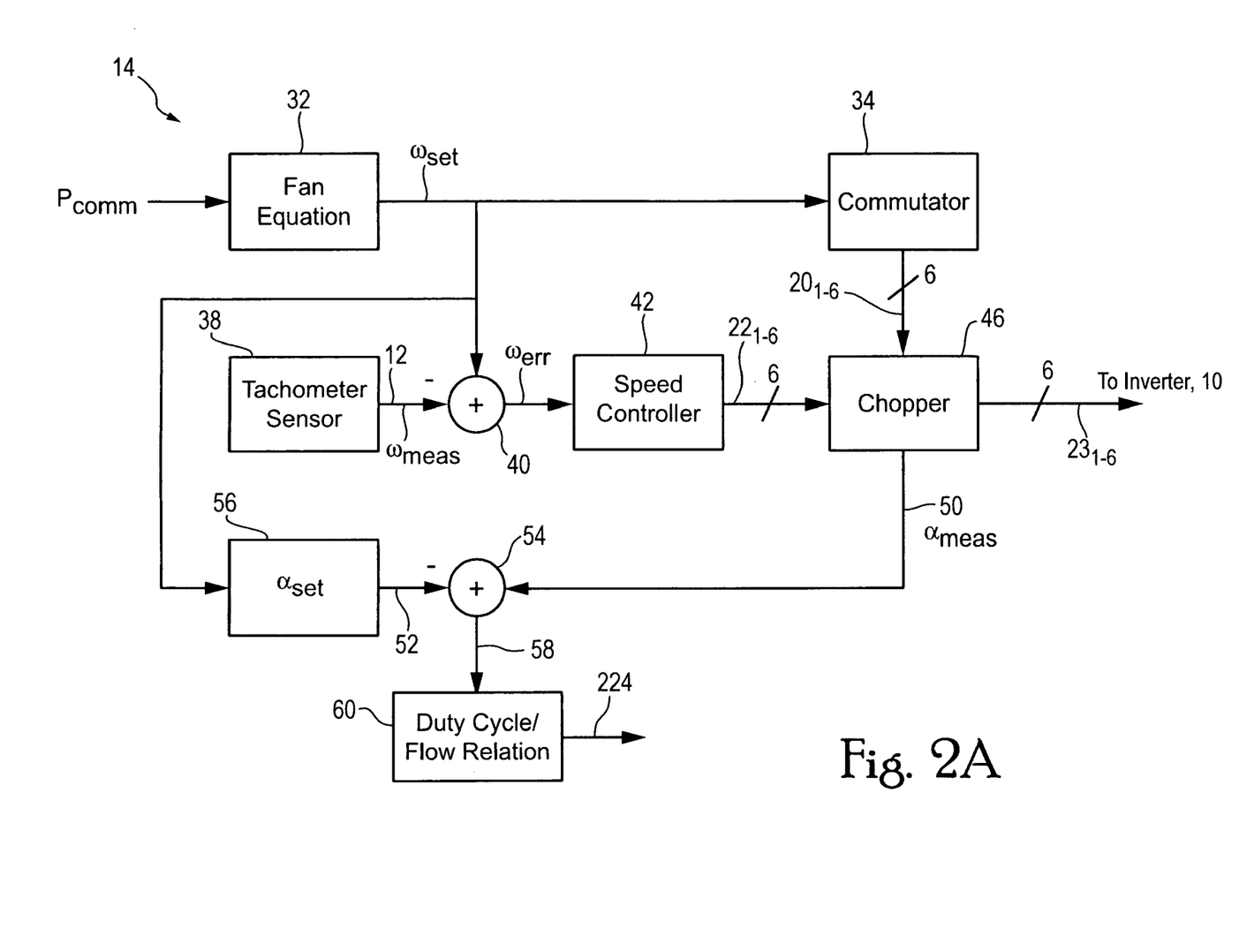
FIG. 2A is a schematic illustration of a controller for the pressure support system of FIG. 1.

With reference to FIG. 2A, and with continuing reference to FIG. 1, the details of the operation of controller 14, inverter 10, and pressure generator 8 are discussed below. Controller 14 receives as an input a pressure command variable $P_{comm}$, which corresponds to the desired or prescribed operating pressure of the pressure support system typically input via input device 18. For example, if the pressure support system is a CPAP system, $P_{comm}$ corresponds to the prescribed CPAP level to be administered to the patient during the pressure support treatment. $P_{comm}$ is typically expressed in units of cmH$_2$O.

It is to be understood, however, that $P_{comm}$ need not remain a single value during the course of the pressure support treatment, but may vary. Varying $P_{comm}$ can be done manually, automatically by the pressure support system itself, or both during the pressure support treatment. For example, in a bi-level pressure support system, there must be two pressure command variables; an inspiratory positive airway pressure (IPAP) $P_{comm(IPAP)}$ and an expiratory positive airway pressure (EPAP) $P_{comm(EPAP)}$. The pressure level delivered to the patient, and, hence, the pressure command variable, changes with the phases of the patient's breathing cycle. The IPAP and EPAP pressures are typically set by a physician and manually input into the pressure support system.

In an auto-titration system, the controller determines the value of $P_{comm}$ according to the auto-titration algorithm used to determine the patient pressure. As a result, the pressure of the flow of gas to be delivered to the patient, which corresponds to $P_{comm}$, can vary over a range of pressures within the maximum and minimum ranges prescribed, depending, for example, on whether or not the patient is experiencing or about to experience disordered breathing.

The pressure command variable $P_{comm}$ can also vary in a CPAP, bi-level, or auto-titration system according to a ramp function, for example, which is commonly used to provide the patient with a relatively low pressure at the outset of the pressure support therapy session, thereby allowing the patient to fall asleep under a relatively lower pressure, and increasing thereafter to the prescribed pressure levels.

Pressure command variable $P_{comm}$ is used by the controller, as illustrated by processing element 32 in FIG. 2A, to determine a rotational speed $\omega_{set}$ in revolutions per minute (rpm) at which the blower must be rotated by the motor in order to produce the pressure specified by the pressure command variable $P_{comm}$. For any desired pressure setting, there is speed at which the blower must be rotated in order to achieve that desired pressure. Controller 14 solves equation (1) below using the pressure command variable $P_{comm}$ to determine a rotational speed $\omega_{set}$ (rpm) for the blower that will result in pressure generator 8 producing in patient circuit 4 the desired fluid pressure $P_{comm}$ in cm H$_2$O:

$$\omega_{set} = \frac{C}{d}\left(\frac{P_{comm}}{\rho}\right), \quad (1)$$

where C is a constant of proportionality, where d is the rotor diameter of the blower in inches, and $\rho$ is the density of gas flowing through the blower (g/cm$^3$), which, as noted above, is typically air from the ambient atmosphere. It can be appreciated from equation (1) that the rotational speed $\omega_{set}$ is a function of the size of the blower, the ambient air density, and the selected pressure $P_{comm}$.

In an exemplary embodiment of the present invention, the rotor diameter of the blower d is set at the time the pressure support system is manufactured based on the actual diameter of the rotor used in that system. The present invention also contemplates setting the density of gas flowing through the blower $\rho$ to a universal value, such as the density of air at sea level. The rotational speed $\omega_{set}$ is thereafter calculated based on these fixed values for d and $\rho$ and based on the input or determined $P_{comm}$ value.

It is to be understood, however, the present invention also contemplates that the density of gas flowing through the blower $\rho$ can be measured directly or determined based on the pressure of the ambient atmosphere. This measured or determined value for the density of gas flowing through the blower $\rho$ can then be used each time $\omega_{set}$ is calculated using equation (1), thereby providing a more accurate determination of the rotational speed of the motor needed to produce the selected pressure than is possible if a universal value for $\rho$ is used.

The rotational speed $\omega_{set}$ of the blower is provided to a commutator 34, which produces drive signals 20 having a pattern and frequency that is sufficient to enable a desired applied torque $T_A$ to be developed by motor 24 for enabling blower 26 to rotate at the speed necessary to produce a desired fluid pressure $P_{comm}$ in patient circuit 4. The pattern and sequence of drive signals 20 is fixed based on the phase angle of the windings in the motor and does not change regardless of the selected pressure $P_{comm}$. However, the frequency or period of drive signals 20 will vary as a function of $\omega_{set}$, so that the rotational speed of motor is sufficient to produce the selected pressure $P_{comm}$.

Controller 14 receives tachometer signals 12 from a tachometer sensor 38 associated with pressure generator 8 or from another tachometer signal source. As noted above, tachometer sensor 38 is any conventional device or method for detecting the rotational speed $\omega_{meas}$ of motor 24 or of blower 26. Controller 14 determines a difference $\omega_{err}$ between the measured tachometer signals 12 $\omega_{meas}$ of the motor and the set rotational speed $\omega_{set}$, as indicated by comparator element 40. Controller 14 then uses this difference $\omega_{err}$ to maintain the operating speed of motor 24 in feedback fashion, as illustrated by a speed controller 42 in controller 14.

More specifically, speed controller 42 produces a control signals $22_{1-6}$ and provides these signals to a chopper portion 46 of controller 14. Chopper portion 46 logically ANDs control signals $22_{1-6}$ and drive signals $20_{1-6}$ to produce switching signals $23_{1-6}$. Thus, control signals $22_{1-6}$ set the duty cycle for switching signals $23_{1-6}$ output from chopper 46. For example, if $\omega_{err}$ is greater than zero, the motor is not rotating fast enough to provide the set pressure $P_{comm}$. As a result, speed controller 42 modifies control signals $22_{1-6}$ to cause an increase in the on-time of the pulses relative to their off-time, i.e., an increase in the duty cycle, of the control signal. This results in an increase in the power provided to the motor as discussed in greater detail below. Conversely, if $\omega_{err}$ is less than zero, the motor is rotating faster than necessary to provide the set pressure $P_{comm}$, and speed controller 42 decreases the duty cycle of control signals $22_{1-6}$, which decreases the duration of the on-time of the pulses in the control signal, thereby reducing the power provided to the motor.

A characteristic 50 of control signals $22_{1-6}$ output by speed controller 42 is compared with a corresponding characteristic 52 associated with the rotating speed $\omega_{set}$ for the motor in a static equilibrium condition, as indicated by comparing element 54 in FIG. 2A. Characteristic 50, which is a function of the duty cycle of the control signals, and characteristic 52, which is associated with the rotating speed $\omega_{set}$ for the motor in a static equilibrium condition, are discussed in detail blow. In short, characteristic 52 is determined by controller 14, as indicated by processing element 56, based on the set rotating speed of the motor when operating in a static equilibrium condition.

A result 58 of this comparison is used to monitor a parameter associated with the fluid flow in patient circuit 4, such as the quantity of flow of fluid in the patient circuit, the direction of the flow of fluid in the patient circuit, the volume of fluid flowing through the patient circuit over a given period of time, or any combination of these parameters. The portion of controller 14 that monitors a parameter associated with fluid flow in patient circuit 4 is illustrated as a duty cycle/flow relation processing element 60. The details of the operation of elements 56, 54, and 60 are discussed below with reference to the schematic diagram illustrated in FIGS. 2A and 2B and with reference to the processing algorithm shown in FIG. 4.

It is to be understood that each element illustrated in FIG. 2A can be a dedicated circuit specifically designed to accomplish the aforementioned functions. However, in a preferred embodiment, each element in FIG. 2A and its associated function corresponds to steps executed by a processor according to a preprogrammed algorithm stored in memory 30. This processor can be any conventional processor having a sufficient processing speed and memory to carry out the motor speed control and flow measuring techniques of the present invention. In an exemplary embodiment of the present invention, processor 14 is a ML4425 motor control integrated circuit manufactured by Fairchild Semiconductor or a MC68HC908MR16 motor control IC manufactured by Motorola.

2. Operation of the Switching Element (Inverter) and Motor

Figure 2B:
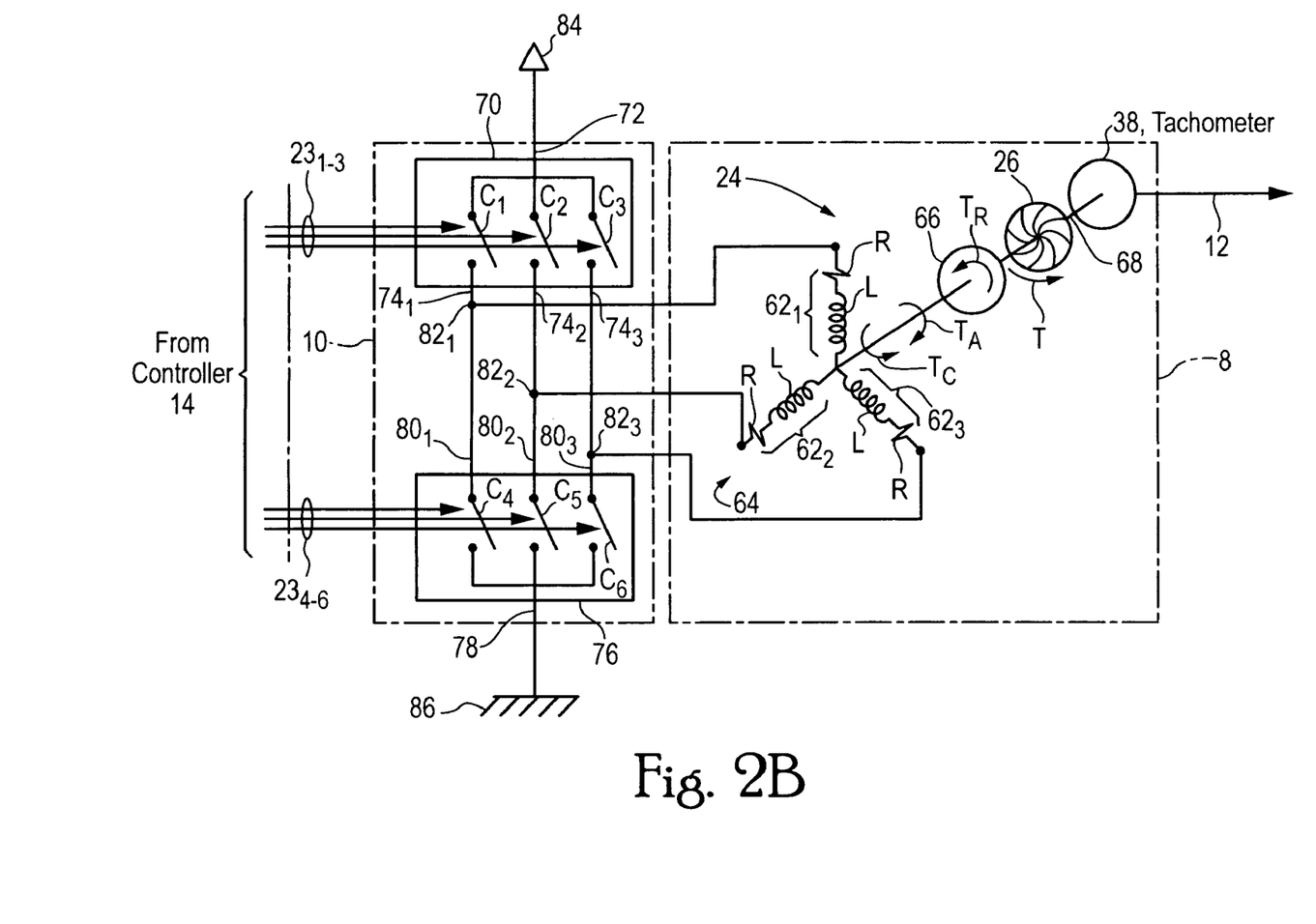
FIG. 2B is a schematic illustration of an inverter and pressure generator for the pressure support system shown in FIG. 1.

As shown in FIG. 2B, switching element 10, which operates as an inverter, receives switching signals $23_{1-6}$ and uses these signals to provide power to pressure generator 8. In the illustrated embodiment, motor 24 in pressure generator 8 has Y-connected phase windings $62_1$–$62_3$ supported by a stationary armature generally indicated at 64. Each phase winding $62_1$–$62_3$ has a resistance R and an inductance L associated therewith. A rotor 66, shown schematically in FIG. 2B, is mounted in a manner known in the art for rotation relative to armature 64. In operation, controller 14 causes inverter 10 to sequentially supply armature current 28 to a first phase winding pair, e.g., $62_1$–$62_2$, a second phase winding pair, e.g., $62_2$–$62_3$, and a third phase winding pair, e.g., $62_1$–$62_3$, in a manner known in the art. Thereafter, the foregoing sequence is repeated. In response to the phase winding pairs sequentially receiving armature current 28, the magnetic interaction of rotor 66 and armature 64 produces an applied $T_A$, which causes rotor 66 to rotate in a first direction.

Motor 24 includes a shaft 68 coupled between rotor 66 and blower 26, which is typically a fan or impeller, disposed in fluid communication with patient circuit 4. In an exemplary embodiment of the present invention, tachometer sensor 38 is coupled to shaft 68 for producing tachometer signal 12, which is provided to controller 14. However, the present invention contemplates incorporating the tachometer function into controller 14, as is known to those skilled in the art. For example, the motor speed can be determined using conventional techniques by monitoring the motor phase voltages at nodes $82_1$, $82_2$ and $82_3$.

Preferably, the values of resistance R and inductance L for each phase winding $62_1$–$62_3$ are selected to meet the current and speed requirements of the motor. An electromotive (EMF) torque $T_C$, which acts on shaft 40 in a direction opposite the applied torque $T_A$, is generated during operation of motor 24. In addition, when rotating, shaft 68 frictionally interacts with stationary components/elements, e.g., bearings (not shown), of armature 64. This frictional interaction generates a resistive torque $T_R$ that also acts on shaft 68 in a direction opposite the applied torque $T_A$.

Lastly, a load torque $T_L$ acts on pressure generator 8 in a direction opposite or the same as applied torque $T_A$ as a result of the viscous friction of the fluid in which blower 26 rotates. Load torque $T_L$ varies as a function of the flow of fluid in patient circuit 4, which will vary, for example, as the patient breathes into the patient circuit or inhales gas from the patient circuit. The existence of this load torque makes it necessary to control the duty cycle of control signal 22 so that the blower is driven at a constant speed $\omega_{set}$. When rotor 66, shaft 68, and blower 26 rotate at constant rotational speed, the sum of the counter EMF torque $T_C$, the resistive torque $T_R$ and the load torque $T_L$ equals the applied torque $T_A$.

Inverter 10 includes a first switching element 70 in the form of a relay, preferably having a plurality of contacts $C_1$–$C_3$ connected between a first pole 72 and a plurality of second poles $74_1$–$74_3$. Inverter 10 also includes a second switching element 76 in the form of a relay, preferably having a plurality of contacts $C_4$–$C_6$ connected between a first pole 78 and a plurality of second poles $80_1$–$80_3$. The second poles $74_1$–$74_3$ of first switching element 70 and the second poles $80_1$–$80_3$ of second switching element 76 are connected together to form a plurality of nodes $82_1$–$82_3$.

Contacts $C_1$–$C_3$ of first switching element 70 are connected to receive switching signals $23_{1-3}$, respectively, and contacts $C_4$–$C_6$ of second switching element 76 are connected to receive switching signals $23_{4-6}$, respectively. Preferably, each contact $C_1$–$C_3$ of first switching element 70 is a transistor having a control input, e.g., a base terminal, connected to receive switching signals $23_{1-3}$, respectively, and each contact $C_4$–$C_6$ of second switching element 76 is a transistor having a control input connected to receive switching signals $23_{4-6}$, respectively.

Phase winding pairs $62_1$–$62_2$, $62_2$–$62_3$ and $62_1$–$62_3$ are connected between respective node pairs $82_1$–$82_2$, $82_2$–$82_3$ and $82_1$–$82_3$. Preferably, first pole 72 of first switching element 70 is connected to a DC power source 84 and first pole 78 of second switching element 76 connected to ground 86. However, first pole 72 can be connected to ground and first pole 78 can be connected to the DC power source.

In operation, controller 14 supplies to inverter 10 switching signals $23_{1-6}$ that cause inverter 10 to sequentially and selectively supply to phase winding pairs $62_1$–$62_2$, $62_2$–$62_3$ and $62_1$–$62_3$ armature current 28, which causes rotor 66 to rotate at the set rotational speed $\omega_{set}$.

Figure 3A:
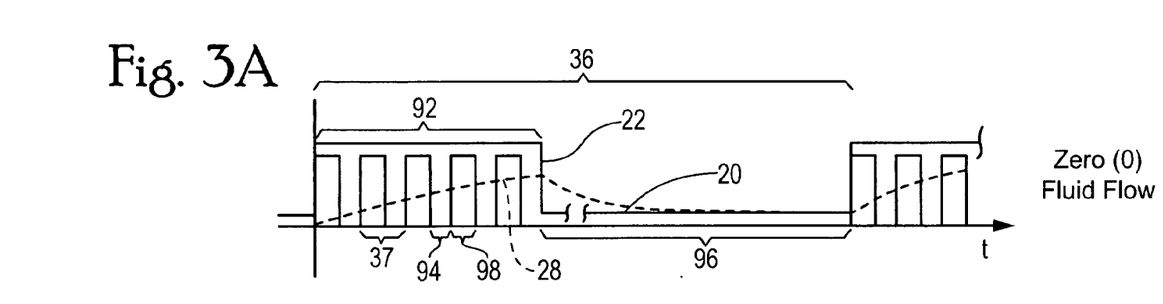
FIGS. 3A–3C show exemplary drive signals and exemplary control signals received by one phase of the inverter of FIGS. 1 and 2 and armature currents supplied thereby in response to receiving the exemplary drive signals and the exemplary control signals.
Figure 3B:
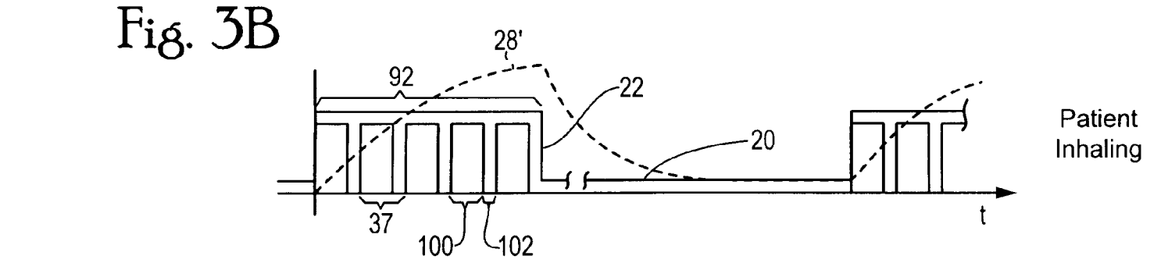
Figure 3C:
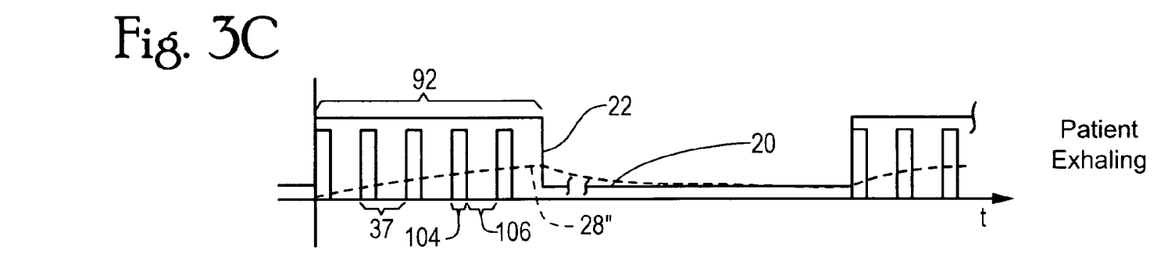

Armature current 28 supplied to phase winding pairs $62_1$–$62_2$, $62_2$–$62_3$ and $62_1$–$62_3$ by drive signals $20_{1-6}$ and control signals $22_{1-6}$ are described with reference to FIGS. 3A–3C. It should be noted that for the sake of simplicity, these figures show only one exemplary drive signal 20, e.g., $20_1$, and one exemplary control signal 22, e.g., $22_2$, that cause inverter 10 to supply armature current 28 to one phase winding pair, e.g., $62_1$–$62_2$. In addition, exemplary drive signal 20 and exemplary control signal 22 in FIGS. 3A–3C are shown offset from each other for illustration purposes. The logical AND of drive signals $20_{1-6}$ and control signals $22_{1-6}$, which occurs in chopper 46, produces switching signals $23_{1-6}$.

It should also be noted that the on and off times of the drive signals and control signals in FIGS. 3A–3C are not drawn to scale. For a three-phase motor, the on time with be ⅓ the duty cycle of the motor, which corresponds to two parts in a six step commutation sequence for a six pole motor, as shown in the figures.

Preferably, for a common pressure setting $P_{comm}$ drive signal 20 is a fixed frequency as per equation (1), having a sequential commutation sequence. On the other hand, control signal 22 is a fixed frequency PWM signal having a variable duty cycle. The variability of the duty cycle of the control signal allows the applied torque to vary in a feedback fashion as the load torque $T_L$ varies, so that the motor attempts to rotate at a speed $\omega_{set}$ corresponding to the selected pressure $P_{comm}$ to be provided to the patient. Control signal 22 has a greater frequency than drive signal 20. The period of drive signal 20 is identified by numeral 36 and the period of control signal 22 is identified by numeral 37 in FIGS. 3A–3C.

As shown in FIG. 3A, control signal 22 has a first duty cycle that is selected so that during a given phase of the motor, the logical AND of drive signals 20 and control signals 22 produces switching signals 23 that cause armature current 28 (shown as a dashed line in FIG. 3A) to flow through the phase winding pair, e.g., $62_1$–$62_2$, connected between DC power source 84 and ground or some common voltage 86 by contacts in first and second switching elements 70 and 76, e.g., contact $C_1$ of first switching element 70 and contact $C_4$ of second switching element 76. Thus, speed controller 42 operates as a means for controlling the speed of the motor by controlling the duty cycle of control signals $22_{1-6}$, and it accomplishes this function in combination in combination with the commutator and the chopper, so that the switching element is actuated properly to operate the motor.

FIG. 3A illustrates a hypothetical no-flow condition, in which there is no flow in patient circuit 4. This is accomplished, for example, by sealing off the flow in patient interface device 5 and plugging exhaust vent 9 or by plugging the patient circuit upstream of the exhaust vent 9. In this no-flow condition, the characteristics of drive signal 20 and control signal 22 are selected so that armature current 28 received by the phase winding pairs causes a sufficient applied torque $T_A$ to be developed to rotate rotor 66, shaft 68 and impeller 26 to produce the desired operating pressure set by $P_{comm}$ and to overcome the counter EMF torque $T_C$ and the resistive torque $T_R$. Because there is no flow in the patient circuit, the load torque $T_L$ is zero.

As represented by the dashed line in FIG. 3A, armature current 28 received by the phase winding pair gradually increases as on-time 94 of control signal 22 increases during the on-time 82 of drive signal 20. This gradual increase is due to the effect of the inductances L of the phase winding pair receiving armature current 28. It should be noted that the dashed line representing the armature current in FIGS. 3A–3C is provided for purposes of illustration and is not intended to be an exact replica of the true armature current. For example, the true armature current would not appear as a smooth line due to the on and off cycles of control signal 22 during an on-time 92 of drive signal 20. Conversely, the inductance of the windings tends to smooth the current waveform.

During an off-time 96 of drive signal 20 for a given phase of the motor, first switching element 70 isolates the phase winding pair from DC power source 84. Hence, the phase winding pair receives no additional armature current during off-time 96 of drive signal 20 regardless of the state of control signal 22. Likewise, during an off-time 98 of control signal 22, for a given phase of the motor, second switching element 77 isolates the phase winding pair from DC power source 84. Hence, the phase winding pair receives no additional armature current.

With reference to FIGS. 2A, 2B, 3A and 3B, during inhalation in which the patient draws fluid from the patient circuit, the load torque $T_L$ experienced by rotor 66, shaft 68, and impeller 26 increases as the motor attempts to keep up the pressure in the patient circuit despite the patient drawing fluid from the circuit. This increase in load torque results in a decrease in the rotational speed of the rotor, which is detected by tachometer sensor 38, and, thus, the difference $\omega_{err}$ becomes greater than zero, i.e., $\omega_{meas} < \omega_{set}$. This positive value for $\omega_{err}$ is transmitted to speed controller 42, which instructs chopper 46 to increase the duty cycle of the control signal 22 sent to inverter 10. This increase in the duty cycle of control signal 22 is illustrated in FIG. 3B as an increase in an on-time 100 of the control signal relative to on-time 94 for the no-flow condition. As a result of this increase in on-time for the constant frequency control signal, more current is provided to the motor, as indicated by the armature current 28' in FIG. 3B having a greater magnitude than that of armature current 28 in FIG. 3A. Of course, the increase in duty cycle can also be understood as a decrease on an off-time 102 of the control signal.

With reference to FIGS. 2A, 2B, 3A and 3C, during exhalation, in which the patient breaths into the patient circuit, the load torque $T_L$ experienced by rotor 66, shaft 68, and impeller 26 decreases as the patient's expiratory effort contributes to the pressure of fluid within the patient circuit so that less pressure is required to be produced by the pressure generator. This decrease in load torque results in an increase in the rotational speed of the rotor, which is detected by tachometer sensor 38, and, thus, the difference $\omega_{err}$ becomes less than zero, i.e., $\omega_{meas} > \omega_{set}$. This negative value for $\omega_{err}$ is transmitted to speed controller 42, which instructs chopper 46 to decrease the duty cycle of the control signal 22 sent to inverter 10. This decrease in the duty cycle of control signal 22 is illustrated in FIG. 3C as a decrease in on-time 104 of the control signal, which again has a constant frequency, so that less current is provided to the motor, as indicated by armature current 28" in FIG. 3C having a smaller magnitude than that of shaded area 28 in FIG. 3A. Of course, the decrease in duty cycle can also be understood as an increase on an off-time 106 of the control signal as shown in FIG. 3C.

The term "duty cycle" used herein refers to the ratio of the "on" time 94, 100, or 104 to "off" time 98, 102 or 106 in control signals 22. Of course, the converse, i.e., the ratio of the "off" time to "on" time, can also be used. In addition, any other unique indication of the duty cycle can be used in the present invention to monitor the control signal. For example, the present invention contemplates using the product of the "on" time and the frequency of the control signal or the switching signal as a characteristic that can be monitored to measure the actual flow in the patient circuit. Because control signals $22_{1-6}$ and switching signals $23_{1-6}$ have a fixed frequency in the present invention, the duty cycle of these signals can also be discussed synonymously in terms of the on-time or the pulsewidth of the "on" portion of the train of pulses. In FIG. 3A, the on-time or pulsewidth of control signal 22 is identified by numeral 94. The on-time of switching signals $23_{1-6}$ is the same as that of control signals $22_{1-6}$, because switching signals $23_{1-6}$ are the logical AND of the control signals and the drive signals. It is also possible to discuss the duty cycle of the control signals and switching signals in terms of the off-time, which is the duration of the "off" portion of these signals.

C. Quantitative Determination of Flow or Volume

It can be appreciated that the duty cycle of control signal 22 is adjusted to maintain the rotational speed of rotor 66, shaft 68, and impeller 26 at the set rotational speed $\omega_{set}$ corresponding to the pressure to be delivered to the patient. It has been empirically determined that for the set rotational speed $\omega_{set}$, the duty cycle or an associated characteristic, such as on-time, of control signals 22 is related to the rate of flow of fluid in patient circuit 4. For example, control signal 22 in FIG. 3B corresponds to a first flow rate in which the patient is drawing fluid from patient circuit 4 and has a duty cycle that is greater than that of the control signal 22 in FIG. 3C, which corresponds to a second flow rate resulting from a patient exhaling into patient circuit 4. By monitoring the duty cycle, on-time, off-time, or other characteristic of the control signal 22 or switching signal 23 uniquely associated with the flow in the patient circuit, controller 14 can determine the rate of flow of fluid flowing in patient circuit 4. Moreover, by monitoring the rate of flow of fluid in patient circuit 4 over an interval of time, controller 14 can determine the volume of fluid inhaled and/or exhaled by patient 6 during that interval.

Figure 4:
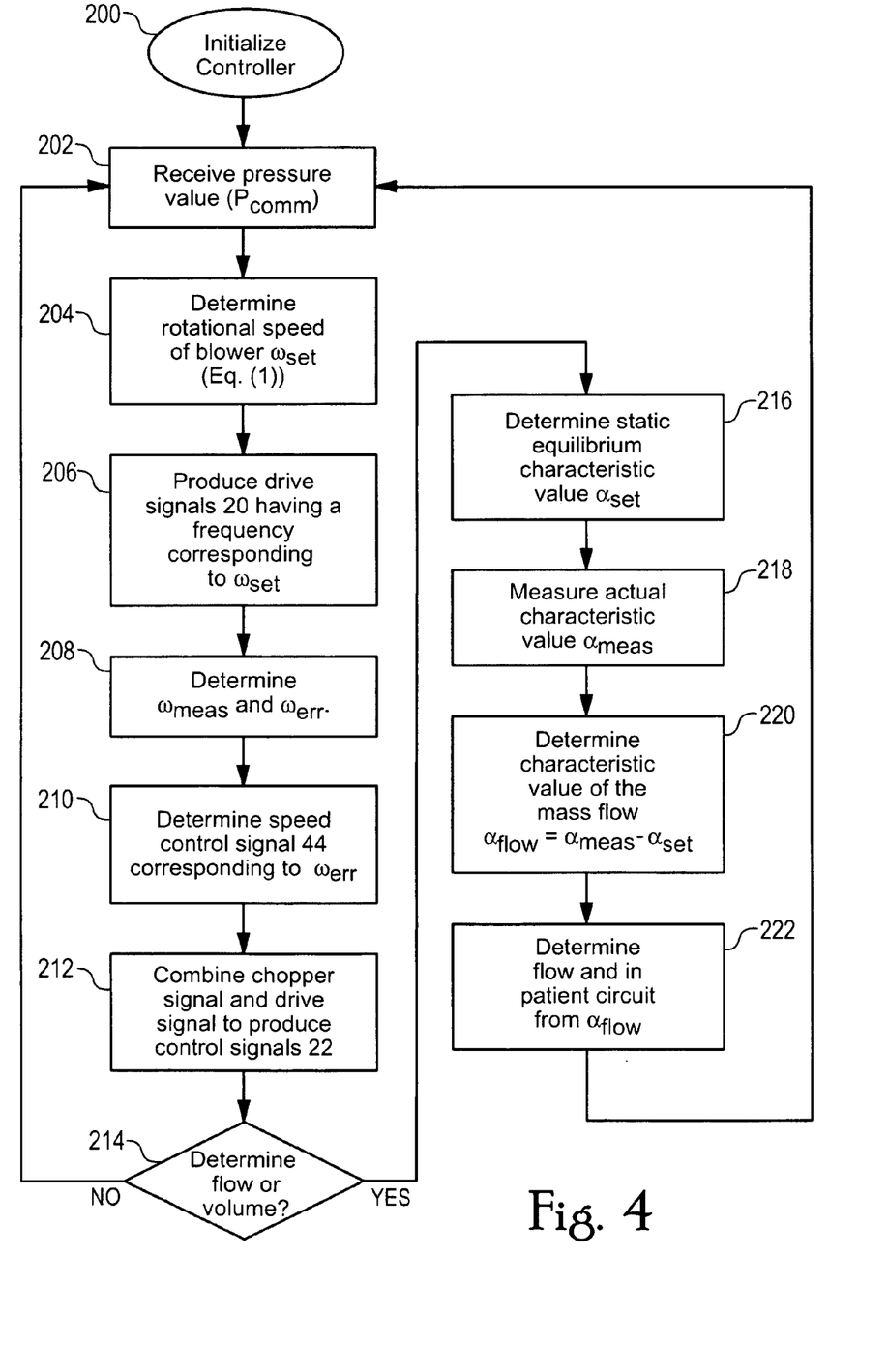
FIG. 4 is a flow diagram of an algorithm for operating the controller shown in FIG. 1.

With reference to FIG. 4, and with continuing reference to FIGS. 1–3C, an exemplary process by which controller 14 generates drive signals 20, control signals 22, and quantitatively determines the flow, volume, or both of fluid flowing in patient circuit 4 under the control of an algorithm, which is resident in memory 26 of controller 14, is discussed below. The process begins in step 200 in which controller 14 is initialized. Thereafter, in step 202, controller 14 obtains from memory 26, keypad 18, or other input device, a pressure command variable $P_{comm}$. The present invention also contemplates that $P_{comm}$ can be determined by other processing routines, as is typically the case on an auto-titration pressure support system, which monitors the patient and either proactively or retroactively controls the pressure to be delivered to the patient by the pressure support system.

In step 204, controller 14 solves equation (1) for the given pressure command variable $P_{comm}$, as discussed above, to determine a rotational speed $\omega_{set}$ for the blower that will result in the pressure generator producing the selected pressure level. Of course, in a bi-level system having an IPAP and an EPAP, two pressure command variables ($P_{comm(IPAP)}$, $P_{comm(EPAP)}$) are provided. The pressure command variable provided to the algorithm of FIG. 4 will depend on whether the patient is determined to be in the inspiratory or the expiratory phase of the breathing cycle.

In step 206, commutator 34 sets the frequency for drive signals 20 that is sufficient to rotate blower 26 at a speed necessary to produce a desired fluid pressure (according to the pressure command variable $P_{comm}$) in patient circuit 4. In step 208, comparator element 40 in controller 14 receives, from tachometer sensor 38, a value $\omega_{meas}$ corresponding to the actual rotational speed of rotor 66 and compares this value to $\omega_{set}$ to obtain difference value $\omega_{err}$.

This difference value is provided, in step 210, to speed controller 42, which produces speed control signal 44 that sets the duty cycle of control signals 22 to maintain the actual rotational velocity of rotor 38 at the set rotational velocity (set. It should be understood that in an exemplary embodiment of the present invention, the frequency of control signals 22 is set to a fixed value based on the selected pressure $P_{comm}$ and the duty cycle of the control signal varies, for example, as the load torque on the impeller varies.

In step 212, chopper 46 in controller 14 logically ANDs control signals $22_{1-6}$ and drive signals $20_{1-6}$ to obtain switching signals 23. In step 214, a decision is made whether the quantitative flow, volume, or both are to be calculated during this processing run. It should be noted that this decision step is optional, because the present invention contemplates automatically calculating the quantitative flow or volume of fluid passing through the patient circuit without any decision required. If the flow, volume or both are to be measured, the process continues to step 216, otherwise it returns to step 202.

Before describing steps 216–222 in FIG. 4 explaining how the present invention quantitatively determines the mass flow of fluid in the patient circuit (or the volume of fluid over time flowing therethrough, which is function of the mass flow over a given period of time), a brief discussion of the background of the flow/volume measurement concept of the present invention is warranted.

If the reluctance terms in the motor are ignored, the applied torque $T_A$ produced in the motor is proportional to the applied or armature current 28. This relationship is expressed as follows:

$$T_A = (K_m)(I_a) \qquad (2)$$

where $K_m$ is the motor or torque constant, and $I_a$ is the armature current 28. When the motor is not accelerating (spinning at a constant speed), referred to as being in a state of static equilibrium, the applied torque is given as follows:

$$T_A = (b)(\dot{\theta}) + T_L, \qquad (3)$$

where b is the viscous friction term of the impeller and $\dot{\theta}$ is the angular velocity of the impeller.

It should be noted that there are two types of static equilibrium situations. The first static equilibrium condition corresponds to that of FIG. 3A, and is referred to as a zero-flow static equilibrium condition, where there is no flow in the patient circuit. This occurs if the patient circuit is plugged upstream of the exhaust element or if the patient interface end and all exhaust ports are blocked. In this zero-flow static equilibrium condition, the motor is not accelerating, and there is no flow of fluid in the patient circuit due to its being blocked.

The second static equilibrium condition is a constant-flow static equilibrium condition, where there is a constant-flow in the patient circuit that does not change. This occurs where there is a constant exhaust from the patient circuit. For example, if the patient circuit is plugged downstream of the exhaust element, there will be a constant, non-varying exhaust flow that exits from the patient circuit via the exhaust element. The invention will be described below first with reference to the zero-flow static equilibrium situation. However, the present invention can also be operated based on the constant-flow static equilibrium condition, as discussed herein following the discussion of the zero-flow static equilibrium condition.

From the relationship given in equation (3) it can be understood that the applied torque $T_A$ will overcome the load torque $T_L$ plus some viscous friction term related to motor speed. If the pressure of the fluid output of the pressure generator remains constant despite variations in the flow in the patient circuit, and assuming the radius of the impeller also remains constant, the load torque is proportional to the mass flow in the patient circuit, as expressed in equation (4):

$$T_L = (C)(\dot{m}), \quad (4)$$

where C is a proportionality constant and $\dot{m}$ is the mass flow of the fluid in the patient circuit.

The former assumption noted above, i.e., that pressure remains constant pressure despite variations in the flow of fluid within the patient circuit, can be satisfied by using an impeller in pressure generator 8 specifically designed to provide a relative constant pressure over a range of flows. Such an impeller is described, for example, in U.S. patent application Ser. No. 09/883,035, to Truitt et al., entitled, "Impeller and Pressure Support System and Method Using Such an Impeller," filed Jun. 15, 2001, the contents of which are incorporated herein by reference.

Combining equations (2),(3), and (4) gives the following new equation:

$$\dot{m} = (C')(I_a) - (b')(\dot{\theta}) \quad (5)$$

where, $$C' = \frac{K_m}{C},$$

and $$b' = \frac{b}{C}.$$

From equation (5) it can be appreciated that the mass flow of fluid in the patient circuit can be determined by the armature current $I_a$ if frictional losses are removed. It can be appreciated that the armature current varies as the mass flow of fluid in the patient circuit varies. For example, as the flow of fluid in the direction indicated by arrow B in FIG. 1 decreases, which occurs when the patient breathes into the patient circuit, the load torque $T_L$ of the motor decreases and the armature current must also decrease, as discussed above. The opposite is true as the flow of fluid increases, for example, when the patient inhales from the patient circuit.

The present inventors recognized that armature current 28 is some function of the duty cycle of the control signal 22. This relation is generally expressed as:

$$I_a = f(\alpha), \quad (6)$$

where α is a characteristic of the control signal. Combining equations (5) and (6) concludes that the mass flow is some function of the duty cycle of control signal 22, which can be empirically determined of calculated for a given set of conditions for motor voltage, $P_{comm}$, and other known factors. The same is true with respect to switching signal 23 due to the fact that switching signal 23 is the logical AND of control signal 22 and drive signal 20.

In a digital system, the pulsewidth or on-time of a signal can be measured by counting the number of clock cycles of the processor that the signal is on during a certain period of time, such as during one period of that signal. For example, the pulses in control signal 22 illustrated in FIG. 3B have on-times 100 that include more clock cycles than the pulses in control signal 22 of FIG. 3A, which have an on-time 94. As noted above, the on-time or pulsewidth of control signals 22 during a commutation state, i.e., during on-times 94, 100, and 104 in FIGS. 3A–3C, determines the amount of energy provided to the motor. In a digital system, measuring or counting the number of clock cycles of an event or a series of events, such as the number of clock cycles of control signals 22 during single period 37, is easily accomplished, and, therefore, represents a convenient technique for measuring on-time. It is to be understood, however, that other techniques for measuring the duration of the on-pulses are contemplated by the present invention.

By exporting the number of clock cycles as characteristic α in equation (6), the number of clock cycles $\alpha_{set}$ that corresponds to the on-time of the control signal required to maintain the motor in zero-flow static equilibrium is determined from the rotating speed $\omega_{set}$. Determining $\alpha_{set}$ from $\omega_{set}$ is accomplished in step 216 in FIG. 4 and is carried out in processing element 56 shown in FIG. 1. Determining $\alpha_{set}$ from $\omega_{set}$ is equivalent to counting the number of clock cycles that occur during the on-time 94 in FIG. 3A, which illustrates the zero-flow static equilibrium condition. It can be appreciated that the number of clock cycles during the on-time can also be counted during each period 37, as the length of each period remains fixed regardless of changes in the pulsewidth.

The present invention contemplates determining the value of $\alpha_{set}$ in advance for different rotating speeds of the motor, and storing a table of values of $\alpha_{set}$ for the values of $\omega_{set}$ or storing a mathematical relationship between $\omega_{set}$ and $\alpha_{set}$. Thereafter, once the desired pressure $P_{comm}$ is set, the appropriate value of $\alpha_{set}$ is recalled from the table or calculated from the stored mathematical relation for that value of $P_{comm}$ (or the corresponding rotating speed $\omega_{set}$) in set 216. For example, the present invention contemplates providing a look-up table or a mathematical relationship describing the correlation between $\omega_{set}$ and $\alpha_{set}$. Once the processor determines $\omega_{set}$, it refers to this look-up table or relationship to determine the appropriate value of $\alpha_{set}$ using any conventional technique. Because there is a known relationship between $P_{comm}$ and $\omega_{set}$, the $P_{comm}$ value can be used in this table or relationship in place of $\omega_{set}$.

According to a second technique, the appropriate value of $\alpha_{set}$ is determined at the time the pressure support system is used rather than in advance. This is accomplished by causing the pressure support system to operate in the zero-flow static equilibrium condition and then counting the number of clock cycles in period 37. Causing the pressure support system to operate in the zero-flow static equilibrium condition is accomplished, for example, by plugging the patient circuit upstream of the exhaust element so that no gas exists from the patient circuit while the pressure generator is running. For example, a plug can be placed at external coupling 7.

An advantage of predetermining the relationship between $P_{comm}$ or $\omega_{set}$ and $\alpha_{set}$ is that it does not require the user to perform the extra steps of causing the pressure support system to operate in the static equilibrium condition. However, it requires that this relationship be determined in advance, storing this relationship in memory, and retrieving the relationship. The latter technique of determining $\alpha_{set}$ using the pressure support system running in the zero-flow static equilibrium condition allows $\alpha_{set}$ to be updated repeatedly. However, this technique relies on the user's ability to perform the zero-flow static equilibrium test accurately.

In step 218 of FIG. 4, the number of clock cycles $\alpha_{meas}$ in control signal 22 during one period 37 (or during the on-time of the control signal) is determined. This number of clock cycles $\alpha_{meas}$ is shown in FIG. 1 as signal 50 output from chopper 46 and corresponds, for example, to the number of clock cycles during on-time 100 (FIG. 3B) or on-time 104 (FIG. 3C). The number of clock cycles $\alpha_{meas}$ corresponds to the amount of energy required to be delivered to the motor in order to deliver the applied Torque $T_A$ needed to produce the selected pressure. Stated another way, $\alpha_{meas}$ corresponds to the number of clock cycles during the on-time of the control signal that is required to overcome the counter EMF torque $T_C$ and the resistive torque $T_R$ and the number of additional clock cycles that are required to maintain the set rotational speed in the nonzero flow conditions, i.e., in the presence of a varying load torque $T_L$. For example, if the load is reduced, which occurs when the patient exhales into the patient circuit, the number of clock cycles required to maintain the set rotational speed is reduced from $\alpha_{set}$, as indicated by on-time 104 in FIG. 3C being less than on-time 94 in FIG. 3A.

In step 220, the number of clock cycles $\alpha_{meas}$ is compared with the number of clock cycles $\alpha_{set}$ that corresponds to the on-time of the motor required to maintain the motor in zero-flow static equilibrium to produce result 58. This step is shown schematically in FIG. 2A as being carried out by comparing element 54. In essence, the result of comparing $\alpha_{meas}$ to $\alpha_{set}$ yields an indication of the number of clock cycles $\alpha_{flow}$ that are added to or removed from the zero-flow static equilibrium control signal to compensate for the load on the motor resulting from the patient breathing into or inhaling from the patient circuit. Thus, $\alpha_{flow}$ is an indication of the change in the control signal from its zero-flow static equilibrium control state resulting from patient induced variations in the flow of gas in the patient circuit.

The present inventors recognized that this change $\alpha_{flow}$ is indicative of the quantitative flow of gas in the patient circuit. Thus, the quantitative flow in the patient circuit is established by developing a relationship between the actual flow in the patient circuit and the changes in the number of clock cycles $\alpha_{flow}$. In an exemplary embodiment of the present invention, controller 14 includes in memory 26 an array of empirically determined fluid flow values associated with the number of clock cycles $\alpha_{flow}$. The present invention also contemplates determining a mathematical relationship between the empirically determined fluid flow values and the associated number of clock cycles $\alpha_{flow}$. In step 222, controller 14 utilizes the number of clock cycles (also referred to as counts) $\alpha_{flow}$ determined in step 220 to obtain from the array, either directly or by interpolation, (or from the mathematical relation) a quantitative fluid flow value 224. This process is shown in FIG. 2A as being carried out by duty cycle/flow relation element 60. Quantitative flow value 224 is used in any conventional manner, examples of which are discussed below.

The use of the deviation between number of clock cycles $\alpha_{meas}$ for the on-time of the control signal and the number of clock cycles $\alpha_{set}$ for the on-time of the control signal in the zero-flow static equilibrium condition to determine quantitatively the actual flow in the patient circuit has been described above. It is to be understood, however, the number of clock cycles of the off-time of the control signal can also be used, because the period of the control signal remains fixed. Also, the duty cycle, i.e., the ratio of the on-time to the off-time, can also be used. That is, the deviation between duty cycle of the control signal and the duty cycle of the zero-flow static equilibrium can be used to determine quantitatively the actual flow in the patient circuit.

The present inventors conducted an experiment to show the relationship between changes in the control signal 22 and the flow Q in the patient circuit for a given set pressure ($P_{comm}$). In this experiment, the system shown in FIGS. 1–2B was used.

The duty cycle of control signal 22 was measured, and the actual flow in the patient circuit was measured using a conventional flow meter. Table 1 below is a chart of the duty cycle of control signal 22 versus the actual flow in liters per minute (1 pm) in the patient circuit.

| Flow Q (lpm) | Duty Cycle (%) |
| --- | --- |
| 0 | 51.14 |
| 9.9 | 52.3 |
| 20.0 | 53.4 |
| 30.0 | 54.0 |
| 40.0 | 54.5 |
| 50.0 | 55.7 |
| 60.0 | 57.0 |

It can be appreciated from Table 1 that the "on-time" or duty cycle of the control signal increased as the flow in the patient circuit increased, as expected.

Table 1 also demonstrates that for a given set operating pressure $P_{comm}$, the flow in the patient circuit can be quantitatively determined from an array or look-up table based on a direct measurement of a characteristic (e.g., on-time, off-time, duty cycle) of the control signal, if this relationship is determined in advance. That is, blocks 56 and 54 in FIG. 2A and steps can be eliminated and the characteristic of the control signal 50 can be used directly to determine flow in the patient circuit quantitatively. Of course, this requires storing a table of such relations in advance for each operating pressure $P_{comm}$ of the pressure support system. This may not be practical if the pressure support system is capable of being operated at a large number of different pressures.

It should be noted that the process described above yields a quantitative flow result 224 that is indicative of the flow in the patient circuit relative to the zero-flow static equilibrium condition. In a typical CPAP system, there will always be a constant exhaust flow from the circuit. Thus, quantitative flow result 224 includes this constant or bias flow, which is analogous to a DC bias in an electrical signal. For some applications, such as when using flow to cycle and trigger between an inspiratory positive airway pressure and an expiratory positive airway pressure, this constant-flow is typically factored out to determine the flow in the patient circuit that is induced solely by the respiratory action of the patient.

The present invention contemplates factoring out this constant exhaust flow beforehand, so that it is not included in quantitative flow result 224. This is accomplished by using the constant-flow static equilibrium condition in step 216 of FIG. 4 to determine $\alpha_{set}$ rather than the zero-flow static equilibrium condition. In which case, quantitative flow result 224 is indicative of purely patient induced flow, because all constant leaks from the patient circuit (intentional or unintentional) are factored out.

In the constant-flow static equilibrium condition, the number of clock cycles $\alpha_{set}$ corresponds to the on-time of the control signal required to maintain the motor in constant-flow static equilibrium, where the flow of fluid in the patient circuit includes the intentional and unintentional leaks therefrom.

In step 220, the number of clock cycles $\alpha_{meas}$ is compared with the number of clock cycles $\alpha_{set}$ that corresponds to the on-time of the motor required to maintain the motor in constant-flow static equilibrium to produce result 58. In this case, the result of comparing $\alpha_{meas}$ to $\alpha_{set}$ yields an indication of the number of clock cycles $\alpha_{flow}$ that are added to or removed from the constant-flow static equilibrium control signal to compensate for the load on the motor resulting from the patient breathing into or inhaling from the patient circuit. Thus, $\alpha_{flow}$ is an indication of the change in the control signal from its constant-flow static equilibrium control state resulting from patient induced variations in the flow of gas in the patient circuit. Because both the constant-flow static equilibrium condition and the measured flow include intentional and unintentional leaks, these leak flows cancel each other out. The result is that the quantitative flow result 224 is indicative of the flow in the patient circuit that is only induced by the actions of the patient and does not include the bias leak flow.

The present invention also contemplates determining the constant-flow static equilibrium condition based on an average rotational speed over a number of respiratory cycles. That is, $\omega_{set}$ is determined as the average rotational speed over a number of respiratory cycles, and $\alpha_{set}$ corresponds to the average on-time of the control signals required to maintain the motor in constant-flow static equilibrium over that number of respiratory cycles. In this situation, the constant exhaust flow is subtracted out of the constant-flow static equilibrium flow when the constant-flow static equilibrium is compared to the measured the measured characteristic $\alpha_{mea}$ and the resulting quantitative determination is purely patient induced flow.

D. Uses of the Quantitatively Determined Flow

As noted above, the present invention contemplates utilizing quantitative flow value 224 in any conventional manner. For example, the flow rate over a period of time can be used to determine the direction of the flow of fluid in the patient circuit or the volume of fluid flow in the patient circuit for that period of time. This enables the pressure support system to determine commonly measured biological parameters, such as tidal volume, minute ventilation, etc.

The quantitative flow can also be used to perform conventional leak estimation and respiratory cycle monitoring. For example, the quantitative flow can be used to determine when a patient commences/terminates inhaling, commences/terminates exhaling, and when the patient is neither inhaling nor exhaling. From these determinations, controller 14 can cause a bi-level pressure support system to cycle and trigger between the IPAP and EPAP pressures. For example, U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., and pending U.S. patent application Ser. No. 09/970,383 to Jafari et al., all teach techniques for differentiating between the inspiratory and expiratory phases of a respiratory cycle, and all of which are incorporated by reference into the present application.

Similarly, the present invention contemplates using the quantitative flow in combination with any conventional technique to calculate the leakage of gas from the pressure support system, which includes intentional leaks from the exhaust vent and unintentional leaks from the mask-patient interface, for example. Of course, this can only be done assuming that the zero-flow static equilibrium condition was used to determine quantitative flow. For example, U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., and pending U.S. patent application Ser. No. 09/436,858 to Truschel, Ser. No. 09/586,054 to Frank et al., and Ser. No. 09/970,383 to Jafari et al., the contents of each of which are incorporated by reference into the present invention, all teach techniques for detecting and estimating leak and managing the delivery of breathing gas to the patient in the presence of leaks.

The present invention further contemplates using quantitative flow as a means to measure patient compliance, which is the actual usage of the pressure support system by the patient. For example, controller 14 can also interpret extended intervals, e.g., two minutes, of no changes of the quantitative flow as an indication that the patient is not fluidly interacting with the patient circuit. When such an extended interval is detected, controller 14 can commence accumulating or marking a time interval indicative that the patient is not fluidly interacting with the patient circuit. Similarly, controller 14 can interpret changes of the quantitative flow associated with a normal breathing cycle of the patient as an indication that he or she is fluidly interacting with the patient circuit and can accumulate or mark a time interval corresponding thereto. From one and/or both of these intervals, the compliance by the patient with a prescribed course of therapy, i.e., the patient's actual use of the pressure support system, can be determined.

The quantitatively determined flow can also be used to control the delivery of fluid to the patient. For example, U.S. Pat. Nos. 5,535,738; 5,794,615; and 6,105,575 all to Estes et al., the contents of which are incorporated herein by reference, disclose a device and method of providing a pressure support therapy to a patient in which the pressure support provided to the patient is a function of the patient flow. This mode of ventilating a patient is commonly referred to as proportional positive airway pressure (PPAP) therapy.

In addition, U.S. Pat. Nos. 5,044,362 and 5,107,830 both to Younes et al., the contents of which are incorporated herein by reference, disclose a device and method of providing a pressure support therapy to a patient in which the pressure support provided to the patient is a function of the patient, which is commonly referred to as proportional assist ventilation (PAV). The PAV mode of ventilation utilizes the patient's flow and volume to determine the pressure to be supplied to their airway. As noted above, patient flow is quantitatively measured according to the principles of the present invention. Therefore, the present invention is suited for use in these modes of pressure support or ventilation.

It can be appreciated that the potential uses for the quantitatively determined flow, volume or both are not limited to the applications noted above. Quite the contrary, the present invention contemplates using the techniques of this invention for determining flow, volume or both in any application where such properties of used. For example, the quantitatively determined flow, volume or both can be used in an auto-titration positive pressure therapy, such as those discussed above in the Background of the Invention section.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pressure support system comprising:
   a motor having a plurality of phase windings;
   a switching element operatively coupled to the plurality of phase windings to selectively supply electrical power from a power source to the plurality of phase windings;
   a blower coupled to the motor, wherein rotation of the blower by the motor elevates a pressure of fluid at an outlet of the blower;
   a patient circuit coupled to the outlet of the blower and adapted to communicate the pressurized fluid with an airway of a patient;
   rotational speed controlling means for maintaining a rotational speed of the motor at a set rotational speed corresponding to a selected pressure for the fluid in the patient circuit, wherein the rotational speed of the motor is maintained at the set rotational speed based on a first signal that controls actuation of the switching element; and
   fluid parameter monitoring means for monitoring a parameter associated with a flow of fluid in the patient circuit based on the first signal produced by the rotational speed controlling means.

2. The pressure support system of claim 1, wherein the first signal has a duty cycle, and wherein the fluid parameter monitoring means monitors the parameter associated with the flow of fluid in the patient circuit based on the duty cycle of the first signal.

3. The pressure support system of claim 1, wherein the parameter associated with the flow of fluid in the patient circuit comprises:
   (1) a quantitative flow of fluid in the patient circuit,
   (2) a direction of flow of fluid in the patient circuit,
   (3) variations in magnitude or direction of the flow of fluid in the patient circuit,
   (4) a volume of fluid flowing through the patient circuit, or
   (5) any combination of items (1)–(4).

4. The pressure support system of claim 1, wherein the rotational speed controlling means comprises:
   speed controlling means for generating a control signal having a duty cycle that is selected so as to maintain a rotational speed of the motor at the set rotational speed corresponding to the selected pressure for the fluid in the patient circuit;
   commutating means for outputting a drive signal that establishes a commutation sequence for actuation of the switching element; and
   chopping means for combining the control signal and the drive signal to produce a switching signal that is provided by to the switching element to control actuation of the switching element, and wherein the control signal or the switching signal corresponds to the first signal produced by the rotational speed controlling means that the fluid parameter monitoring means uses to monitor a parameter associated with a flow of fluid in the patient circuit.

5. The pressure support system of claim 1, further comprising:
   means for differentiating between an inspiratory phase and an expiratoy phase of a patient's breathing cycle based on an output of the fluid parameter monitoring means; and
   means for providing a first selected pressure for the fluid in the patient circuit during the inspiratory phase by maintaining the rotational speed of the motor at a first set rotational speed corresponding to the first selected pressure, and for providing a second selected pressure for the fluid in the patient circuit during the expiratory phase by maintaining the rotational speed of the motor at a second set rotational speed corresponding to the second selected pressure.

6. The pressure support system of claim 1, wherein the fluid parameter monitoring means includes:
   abnormal breathing detecting means for determining whether such a patient is experiencing, or is about to experience, disordered breathing based on the parameter associated with the flow of fluid in the patient circuit; and
   pressure adjusting means for altering the selected pressure for the fluid communicated to such a patient by altering the set rotational speed of the motor responsive to an output of the disordered breathing detecting means.

7. The pressure support system of claim 1, further comprising patient compliance monitoring means for determining, based on an output of the fluid parameter monitoring means, whether a patient is using the pressure support system.

8. The pressure support system of claim 7, wherein the compliance monitoring means further comprises means for determining an amount of time that a patient had used the pressure support system.

9. The pressure support system of claim 1, further comprising an input device for entering the selected pressure to the rotational speed controlling means.

10. A pressure support system comprising:
    a motor having a plurality of phase windings;
    a switching element operatively coupled to the plurality of phase winding and adapted to selectively supply electrical power from a power source to the phase windings of the motor;
    tachometer sensing means for measuring a rotational speed of the motor and for outputting a tachometer signal indicative thereof;
    a blower coupled to the motor, wherein rotation of the blower by the motor elevates a pressure of fluid at an outlet of the blower;
    a patient circuit coupled to the outlet of the blower and adapted to communicated the pressurized fluid with an airway of a patient;
    processing means for comparing the tachometer signal to a reference motor speed signal corresponding to a selected pressure for the fluid in the patient circuit and for producing a rotational speed error signal based on a result of the comparison;

a speed controller circuit operatively coupled to the processing means such that the speed controller circuit produces a control signal having a characteristic that varies based on the rotational speed error signal, so that the motor operates at a set rotational speed that corresponds to the selected pressure for the fluid in the patient circuit, and wherein the control signal controls actuation of the switching element; and fluid parameter monitoring means for monitoring a parameter associated with a flow of fluid in the patient circuit based on the characteristic of the control signal.

11. The pressure support system of claim 10, wherein the characteristic of the control signal is a duty cycle of the control signal, and wherein the fluid parameter monitoring means monitors the parameter associated with the flow of fluid in the patient circuit based on the duty cycle of the control signal.

12. The pressure support system of claim 10, wherein the fluid parameter monitoring means monitors the parameter associated with the flow of fluid in the patient circuit by comparing the duty cycle of the control signal with a duty cycle of a zero-flow control signal needed to drive the motor at the set rotational speed where there is no flow in the patient circuit.

13. The pressure support system of claim 10, wherein the fluid parameter monitoring means monitors the parameter associated with the flow of fluid in the patient circuit by comparing the duty cycle of the control signal with a duty cycle of a constant-flow control signal needed to drive the motor at the set rotational speed where there is constant flow in the patient circuit.

14. The pressure support system of claim 10, wherein the parameter associated with the flow of fluid in the patient circuit comprises:
(1) a quantitative flow of fluid in the patient circuit,
(2) a direction of flow of fluid in the patient circuit,
(3) variations in magnitude or direction of flow of fluid in the patient circuit,
(4) a volume of fluid flowing through the patient circuit, or
(5) any combination of items (1)–(4).

15. The pressure support system of claim 10, further comprising:
a commutator circuit that outputs a drive signal based on the reference motor speed signal; and
a chopping circuit that combines the control signal and the drive signal to produce a switching signal, wherein the switching signal is provided by to the switching element to control actuation of the switching element, and wherein the fluid parameter monitoring means monitors the parameter associated with the flow of fluid in the patient circuit based on the characteristic of the control signal or the switching signal.

16. The pressure support system of claim 10, further comprising:
means for differentiating between an inspiratory phase and an expiratoy phase of a patient's breathing cycle based on an output of the fluid parameter monitoring means; and
means for providing a first selected pressure for the fluid in the patient circuit during the inspiratory phase by maintaining the rotational speed of the motor at a first set rotational speed corresponding to the first selected pressure, and for providing a second selected pressure for the fluid in the patient circuit during the expiratory phase by maintaining the rotational speed of the motor at a second set rotational speed corresponding to the second selected pressure.

17. The pressure support system of claim 10, wherein the fluid parameter monitoring means includes:
abnormal breathing detecting means for determining whether such a patient is experiencing, or is about to experience, disordered breathing based on the parameter associated with the flow of fluid in the patient circuit; and
pressure adjusting means for altering the selected pressure for the fluid communicated to such a patient by altering the set rotational speed of the motor responsive to an output of the disordered breathing detecting means.

18. The pressure support system of claim 10, further comprising patient compliance monitoring means for determining, based on an output of the fluid parameter monitoring means, whether a patient is using the pressure support system.

19. The pressure support system of claim 18, wherein the compliance monitoring means further comprises means for determining an amount of time that a patient had used the pressure support system.

20. The pressure support system of claim 10, further comprising an input device for entering the selected pressure to the processing means.

21. The pressure support system of claim 10, wherein fluid parameter monitoring means quantitatively determines a value of a parameter associated with the flow of fluid in the patient based on a stored relation between such a parameter and the duty cycle of the control signal, wherein the stored relation is predetermined empirically.

22. A pressure support system comprising:
a motor having a plurality of phase windings;
a switching element operatively coupled to the plurality of phase winding and adapted to selectively supply electrical power from a power source to the phase windings of the motor;
tachometer sensing means for measuring a rotational speed of the motor and for outputting a tachometer signal indicative thereof;
a blower coupled to the motor, wherein rotation of the blower by the motor elevates a pressure of fluid at an outlet of the blower;
a patient circuit coupled to the outlet of the blower and adapted to communicated the pressurized fluid with an airway of a patient;
processing means for comparing the tachometer signal to a reference motor speed signal corresponding to a selected pressure for the fluid in the patient circuit and for producing a rotational speed error signal based on a result of the comparison;
a speed controller circuit operatively coupled to the processing means such that the speed controller circuit produces a control signal having a characteristic that varies based on the rotational speed error signal;
a commutator circuit that outputs a drive signal based on the reference motor speed signal;
a chopping circuit that combines the control signal and the drive signal to produce a switching signal, wherein the switching signal is provided by to the switching element to control actuation of the switching element; and
fluid parameter monitoring means for monitoring a parameter associated with a flow of fluid in the patient circuit based on the characteristic of the switching signal.

23. The pressure support system of claim 22, wherein the characteristic of the switching signal is a duty cycle of the switching signal, and wherein the fluid parameter monitoring means monitors the parameter associated with the flow of fluid in the patient circuit based on the duty cycle of the switching signal.

24. The pressure support system of claim 22, wherein the fluid parameter monitoring means monitors the parameter associated with the flow of fluid in the patient circuit by comparing the duty cycle of the switching signal with a duty cycle of a zero-flow control signal needed to drive the motor at the set rotational speed where there is no flow in the patient circuit.

25. The pressure support system of claim 22, wherein the fluid parameter monitoring means monitors the parameter associated with the flow of fluid in the patient circuit by comparing the duty cycle of the switching signal with a duty cycle of a constant-flow control signal needed to drive the motor at the set rotational speed where there is constant flow in the patient circuit.

26. The pressure support system of claim 22, wherein the parameter associated with the flow of fluid in the patient circuit comprises:

(1) a quantitative flow of fluid in the patient circuit,
(2) a direction of flow of fluid in the patient circuit,
(3) variations in magnitude or direction of flow of fluid in the patient circuit,
(4) a volume of fluid flowing through the patient circuit, or
(5) any combination of items (1)–(4).

\* \* \* \* \*